(12) United States Patent
Kreczinski et al.

(10) Patent No.: US 8,822,726 B2
(45) Date of Patent: Sep. 2, 2014

(54) METHOD FOR PRODUCING DIAMINODIPHENYL ALKANES

(75) Inventors: Manfred Kreczinski, Herne (DE); Gerda Grund, Coesfeld (DE)

(73) Assignee: Evonik Degussa GmbH, Essen (DE)

( * ) Notice: Subject to any disclaimer, the term of this patent is extended or adjusted under 35 U.S.C. 154(b) by 374 days.

(21) Appl. No.: 12/866,833

(22) PCT Filed: Mar. 10, 2009

(86) PCT No.: PCT/EP2009/052768
§ 371 (c)(1),
(2), (4) Date: Aug. 9, 2010

(87) PCT Pub. No.: WO2009/132883
PCT Pub. Date: Nov. 5, 2009

(65) Prior Publication Data
US 2010/0317893 A1    Dec. 16, 2010

(30) Foreign Application Priority Data
Apr. 30, 2008 (DE) .................. 10 2008 001 469

(51) Int. Cl.
*C07C 209/78* (2006.01)

(52) U.S. Cl.
CPC .................. *C07C 209/78* (2013.01)
USPC ....................................... 564/332

(58) Field of Classification Search
USPC ............... 564/332; 560/338; 562/11
See application file for complete search history.

(56) References Cited

U.S. PATENT DOCUMENTS

| | | | |
|---|---|---|---|
| 4,554,378 A * | 11/1985 | Nafziger et al. | 564/332 |
| 6,649,798 B2 * | 11/2003 | Klein et al. | 564/332 |
| 2011/0021741 A1 * | 1/2011 | Chen et al. | 528/422 |

OTHER PUBLICATIONS de Angelis, A. et al., "Solid acid catalysts for industrial condensations of ketones and aldehydes with aromatics," Ind.Eng.Chem.Res. (2004) 43: 1169-1178.*
AMBERLYST 15Wet Technical Data Sheet (2003), Rohm & Haas.*
Rohm & Haas, Amberlyst 15WET Technical Data Sheet, 2003, p. 1-4 (already of record).*
Siril, P. F. et al., "New Polystyrene Sulfonic Acid Resin Catalysts With Enhanced Acidic and Catalytic Properties", Journal of Molecular Catalysis A: Chemical 279, vol. 279, No. 1, pp. 63-68 (Oct. 7, 2007) XP-022376501.
International Search Report issued Dec. 3, 2009 in PCT/EP09/52768 filed Mar. 10, 2009.
U.S. Appl. No. 12/922,280, filed Sep. 13, 2010, Grund, et al.
U.S. Appl. No. 12/867,168, filed Aug. 11, 2010, Grund, et al.
Chinese Office Action in corresponding Application No. 200910137857.7 dated Mar. 7, 2013.
A. de Angelis, et al., , Ind. Engl. Chem. Res., vol. 43, No. 5, pp. 1169-1178, dated 2004.

* cited by examiner

*Primary Examiner* — Jafar Parsa
*Assistant Examiner* — Amy C Bonaparte
(74) *Attorney, Agent, or Firm* — Oblon, Spivak, McClelland, Maier & Neustadt, L.L.P.

(57) ABSTRACT

The invention relates to a method for producing diaminodiphenyl alkanes, wherein an aromatic amine, which can be substituted or unsubstituted, is reacted with a C1-C3 aldehyde in the presence of a heterogeneous catalyst, said catalyst being a mesoporous acidic ion exchanger based on a divinylbenzene/styrene copolymer and the catalyst having acid centers in a concentration of 2 to 6 eq/kg measured according to DIN 54403 and the average pore diameter of the catalyst particles being 10 to 32 nm measured according to ASTM D 4222, and the content of polynuclear compounds in the reaction mixture being >10 and ~15% by weight.

23 Claims, No Drawings

METHOD FOR PRODUCING DIAMINODIPHENYL ALKANES

BACKGROUND OF THE INVENTION

1. Field of the Invention

The invention relates to a process for preparing bis(aminophenyl)alkanes (alternatively referred to as diaminodiphenylalkanes herein), especially bis(aminophenyl)methane (alternatively referred to as diaminodiphenylmethane herein).

2. Description of the Background Art

The preparation of bis(aminophenyl)alkanes by condensation of an aromatic amine such as aniline and aldehyde over acidic catalysts is known.

In the reaction, first of all, N-alkyl compounds are formed from an aromatic amine (aniline) and aldehyde. These preliminary condensation products then undergo further reaction, in the presence of acidic catalysts, to form aminals. These aminals subsequently undergo rearrangement, under the action of an acidic catalyst, to form bis(aminophenyl) alkanes.

The reaction produces various isomers of the bis(aminophenyl)alkanes. Mixtures of 2,2'-, 2,4'- and 4,4'-bis(aminophenyl)alkanes are formed. Also formed, as by-products, are higher condensation products having three to six nuclei, and also N-alkyl compounds.

According to the known state of the art, the bis(aminophenyl)alkanes obtained are processed further to form diisocyanates such as, for example, diisocyanato-dicyclohexylmethane or diisocyanatodiphenylmethane, or other diisocyanates. These compounds are important paint base materials and base products for, for example, the preparation of polyurethanes.

In the prior art, bis(aminophenyl)alkanes have frequently been prepared from the condensation of aniline and aldehyde, especially aniline and formaldehyde. In that reaction, according to its particular variant, either first the condensation product of aniline and formaldehyde has been prepared and has then been subjected to rearrangement in the presence of acids such as hydrochloric acid, for example, or else the condensation itself has been carried out in the presence of acids, under rearrangement conditions.

A disadvantage of this approach is that, in the case of homogeneous catalysis with mineral acids, salt-containing wastewaters are produced which are formed on neutralization of the acids. Furthermore, the aqueous mineral acids lead to corrosion problems in the production plants. Consequently, in further prior art, processes have been developed which use corresponding heterogeneous catalysts. In these processes, in addition to acidic ion-exchangers, acidic synthetic or natural silicon oxides or aluminium oxides are used as well, such as zeolites or clay minerals.

In U.S. Pat. No. 4,294,981, in a process of this kind, the condensation is carried out in the presence of a strong aqueous acid, the acid being subsequently removed by solvent extraction. The rearrangement is carried out in turn in the presence of a strong acid, which is used in a relatively small amount. Diatomaceous earth, clays or zeolites can be used as catalysts in this reaction stage.

DE-A-12 30 033 describes a process for preparing bis(aminophenyl)alkanes. It uses silicon-containing clay, a synthetic silicon dioxide-aluminium oxide catalyst or a magnesium oxide-aluminium oxide catalyst.

Another reaction process for preparing bis(aminophenyl) alkanes is described in DE-A-14 93 431. The catalyst it uses is silicon dioxide, silicon dioxide-aluminium oxide or acid-treated aluminium oxide. Preference is given to silica gel or bentonite-like clay which contains silicon dioxide and aluminium oxide and is preferably acid-activated.

U.S. Pat. No. 4,071,558 describes a preparation process for preparing bis(aminophenyl)alkanes wherein an acid-activated clay catalyst, a silicon dioxide-aluminium oxide-containing cracking catalyst or a silicon dioxide-magnesium oxide catalyst is used.

U.S. Pat. No. 4,039,580 describes a preparation process in which the condensation of aniline and formaldehyde is performed in the absence of a catalyst and then the condensation product is subjected to further reaction in the presence of diatomaceous earth, clays or zeolites to form bis(aminophenyl)methane. Similar reactions are also described by U.S. Pat. No. 4,039,581.

The catalysts from the group of magnesium oxides or aluminium oxides, clay catalysts or silicon dioxide catalysts have not become established, owing to their high prices, low activities, inconsistent quality and inadequate service lives.

In the more recent prior art, therefore, the proposal is made to prepare bis(aminophenyl)alkanes using as the catalyst an ion-exchanger which possesses acidic groups. EP 0 043 933 A1, for instance, describes a process for preparing polyamine mixtures having a high fraction of 4,4'-diaminodiphenylmethane and a low fraction of 2,4'-diaminodiphenylmethane, in which the catalyst used is an ion-exchanger based on a divinylbenzene/styrene copolymer. This ion-exchanger possesses sulphonic acid groups, a specific surface area of 2 to 40 $m^2/g$ and a pore size of 0.5 to 40 nm. Acidic groups used for the catalyst are sulphonic acid groups. The yields in this process are situated in the range from 60% to 78%. With the sulphonated styrene-divinylbenzene copolymer catalyst it is possible to prepare diaminodiphenylmethanes which possess a high 4,4'-diaminodiphenyl-methane content. The latter isomer is needed in particular for further processing, namely for reaction to form corresponding diisocyanates of the diphenylmethane series, which represent the starting materials in the preparation of polyurethanes or are used as paint base materials. The publication further describes how the fraction of 2,2'- and 2,4'-diisocyanatodiphenylmethane compounds must be extremely low, since for numerous fields of application in the polyisocyanate sector these isomers are unwanted. According to the prior art EP 0 043 933, the resulting diaminodiphenylmethane compounds are immediately subjected to a phosgenation to prepare corresponding diisocyanates.

The process described in EP 0 043 933 for preparing bis (aminophenyl)alkanes has the disadvantage that it possesses low yields and that, in spite of a high reaction temperature, very long reaction times are needed in order to achieve an industrially acceptable yield. A further disadvantage is that the prior-art process produces only a small fraction of 2,4' isomer.

As well as aromatic isocyanates, the corresponding aliphatic isocyanates are particularly important in certain speciality sectors.

The next stage in the operation of preparing aliphatic isocyanates is the hydrogenation of the aromatic ring of the bis(aminophenyl)alkanes.

The hydrogenation of diaminodiphenylmethane produces, from the 4,4' isomer, the 4,4' trans/trans-, cis/cis- and cis/trans-diaminodicyclohexylmethane (PACM). The trans/trans-4,4'-diaminodicyclohexylmethane content has a considerable influence on the crystallization propensity of the diisocyanate. If the trans/trans 4,4' fraction of the diisocyanate product prepared from PACM by phosgenation or other processes is too high, the diisocyanatodicyclohexylmethane may form crystals even at room temperature, which is a hindrance to its further processing to form polyurethanes.

Prior to the further processing, therefore, costly and inconvenient process steps must be undertaken in order to reduce the 4,4' isomer content to an acceptable level, so that crystallites are no longer formed. This is usually accomplished by increasing the concentration of the 2,4' isomer.

A further requirement concerning the isomer content in the preparation of diaminodiphenylmethane is that there must be as small as possible a fraction of 2,2' isomer present, since this isomer causes chain termination in the polymerization reaction during the subsequent step of processing to form polyurethanes. In order to avoid this additional cost and complexity, it is important, for this reaction route, to obtain a defined isomer ratio during the preparation of the diaminodiphenylmethane itself.

According to the state of the art to date, this isomer ratio is obtained by the costly and inconvenient procedure of purifying and distilling the diaminodiphenylmethane in order to be able to provide the isomers in the ratio needed for further processing.

SUMMARY OF THE INVENTION

The technical problem addressed by the invention, therefore, is that of providing a process for preparing bis(aminophenyl)alkanes that leads directly to the specific isomer ratio required for further processing to the aliphatic diisocyanate and for the corresponding reaction to form polyurethanes. A further technical problem addressed by the invention is that of developing a process which operates more economically in requiring a shorter reaction time and leading to the desired isomer yields. At the same time the formation of salt-loaded wastewater is also to be avoided.

This technical problem is solved by a process for preparing bis(aminophenyl)alkanes, where an aromatic amine, which may be substituted or unsubstituted, is reacted with a $C_1$-$C_3$ aldehyde in the presence of a heterogeneous catalyst, the catalyst being a mesoporous acidic ion-exchanger based on a divinylbenzene/styrene copolymer, and the catalyst having acidic centres, measured in accordance with DIN 54 403, in a concentration of 2 to 6 eq/kg, and the average pore diameter of the catalyst particles, measured in accordance with ASTM D 4222, being 10 to 32 nm, and the polynuclear compound content of the reaction mixture formed being >10% and ≤15% by weight.

DETAILED DESCRIPTION OF THE INVENTION

In one preferred embodiment the concentration of the acidic centres of the ion exchanger is 4.4 to 5.7 eq/kg (eq/kg means equivalents per kilogram of ion exchanger) and very preferably 4.7 to 5.6 eq/kg, measured in accordance with DIN 54 403.

The acidic centres are preferably acid groups and more preferably sulphonic acid groups.

By mesoporous ion exchangers are meant those which possess an average pore diameter, measured in accordance with ASTM D 4222, of 2 to 50 nm. In accordance with the invention, however, mesoporous ion exchangers having an average pore diameter of the catalyst particles, measured in accordance with ASTDM D 4222, of 10 to 32 nm are used.

The pore diameter of the ion exchangers, measured in accordance with ASTM D 4222, is preferably 15 up to and including 30 nm and very preferably 22 up to and including 30 nm.

The properties of these resins, more particularly specific surface area, porosity, stability and exchange capacity, can be varied by means of the preparation process. Thus, for example, the size of the pores and their distribution is influenced by addition of porogens. Porogens are inert organic substances, is solvents or precipitants for example, which during the free-radical suspension polymerization are not included in the polymerization process. After the polymerization they are removed from the polymer again, and are responsible, together with the crosslinker fraction, for the degree of porosity. Porogens serve as solvents for the monomers and as precipitants for the resultant polymers. Porogens used in suspension polymerization include, for example, isopropanol, toluene, heptane, paraffin wax, benzine, amyl alcohol or nitromethane.

Use may be made of acidic resins of the divinylbenzene/styrene copolymer that are sold under the following trade names: DUOLITE, AMBERLYST, AMBERLITE, DOWEX, LEWATIT.

Formaldehyde is used preferably as aldehyde. Formaldehyde may be used in the form of aqueous formalin solution or else as formaldehyde in gaseous form. Additionally it is also possible to use compounds which give off formaldehyde under the reaction conditions, such as trioxymethylene or paraformaldehyde, for example. For the reaction it is preferred to use an aqueous formalin solution. Aromatic amines used may be substituted or unsubstituted amines. Preferably the amines, if they are substituted, ought not to possess any substituents in paraposition. Examples of suitable aromatic amines are N-methylaniline, N-ethylaniline, o-toluidine, o-chloroaniline, m-chloroaniline, o-anisidine, 2,3-xylidine, 3,5-xylidine, o-cyclohexylaniline, o-benzylaniline, alpha-naphthylaniline, methylmercaptoaniline or aniline. Particular preference is given to the use of aniline as aromatic amine.

In the preparation process of the invention the following composition and isomer ratios are obtained, preferably distributed as follows:
64% to 85% by weight 4,4' bis(aminophenyl)alkane,
3% to 20% by weight, preferably 7% to 17% by weight, 2,4' bis(aminophenyl)alkane
and
≥1% to ≤2% by weight 2,2' bis(aminophenyl)alkane.

With the process of the invention it is preferred to prepare diaminodiphenyl-methane with the following isomer composition:
64% to 85% by weight 4,4' bis(aminophenyl)methane,
3% to 20% by weight, preferably 7% to 17% by weight, 2,4' bis(aminophenyl)methane
and
≥1% by weight to ≤2% by weight 2,2' bis(aminophenyl)methane.

The fraction of polynuclear compounds in the isomer mixture of the bis(aminophenyl)alkane, more particularly of diaminodiphenylmethane, is >10% by weight to ≤15% by weight, preferably <15% by weight. Polynuclear compounds for the purposes of the invention are those molecules having more than two aromatic nuclei, more particularly phenyl rings.

The N-methyl compound impurities in the isomer mixture of the bis(aminophenyl)alkane, more particularly of diaminodiphenylmethane, more particularly diaminodiphenylmethane, are ≤1.0% by weight, preferably ≤0.5% by weight and more preferably ≤0.3% by weight.

This isomer distribution is particularly suitable for further processing via diaminodicyclohexylmethane to the corresponding diisocyanatodicyclohexylmethane compound. The isomer ratio obtained in the process of the invention also determines the subsequent isomer ratio in the diisocyanate compound.

With the process of the invention the required isomer ratio is obtained at the bis(aminophenyl)alkane, more particularly of diaminodiphenylmethane preparation stage itself, without having to be brought about by means of additional separation processes, which are inconvenient and expensive. Moreover, such purification processes are a disadvantage in view of the fact that the substances involved are very reactive, and so possible side reactions may occur in the course of purification or distillation.

A further advantage of the process of the invention is that the fraction of unwanted by-products, especially N-methyl compounds, is very low. On further processing to the diisocyanate, N-methyl compounds lead to unwanted monoisocyanates and hence to a deterioration in the quality of the product.

The prior-art processes operating with acidic ion exchangers as catalysts lead to significantly higher isomer fractions of 4,4' bis(aminophenyl)alkane. For instance, in the examples of publication EP 0 043 933, the corresponding amounts are 94%, 92% and 91% by weight. These isomer contents, however, are too high, since the further processing to form the aliphatic diisocyanate compound is accompanied by crystallization, which is unwanted.

The bis(aminophenyl)alkanes obtained according to EP 0 043 933 must therefore be brought by means of additional process steps, such as distillation, to the desired isomer ratio of 64% to 85% by weight 4,4'-diaminodiphenylalkane, 3% to 20% by weight 2,4'-diaminodiphenylalkane and ≥1.0% to ≤2% by weight 2,2'-diaminodiphenylalkane.

A further advantage of the process of the invention lies in its environmental and economic performance. The catalytic reaction is performed preferably at a reaction temperature in the range from 80 to 140° C., more preferably 80 to 130° C. and very preferably 80 to 120° C. The required reaction time for the catalytic reaction is preferably 30 minutes to 5 hours, more preferably 0.75 hour to 4.5 hours and very preferably 0.75 to 3.0 hours.

These reaction times are considerably lower in comparison to EP 0 043 933. From the examples of the publication it is apparent that the reaction times there are up 15 to 20 hours and are therefore around twenty times higher than in the case of the process of the present invention. The reaction temperature is similarly high, and this implies an approximately twentyfold higher energy consumption for the implementation of the reaction.

The process of the invention therefore possesses the advantage that it can be carried out less expensively and more economically and also, by virtue of the shorter reaction time, affords a greater conversion per unit time.

The yields in the process of the invention as well are higher than in the prior art. Thus the yields according to EP 0 043 933 in the examples are situated in the range from 60% to 78% by weight. In comparison to this, in the case of the process of the present invention, overall yields of 80% to 95% by weight are obtained, as defined in the examples.

The starting substances used are preferably aromatic amine and aldehyde in a molar ratio of 5:1 to 15:1, preferably 7:1 to 12:1 and very preferably 10:1. It is preferred to use the amine in excess, since this increases the selectivity. Excess amine can be removed by distillation after the conclusion of the reaction.

Catalysts used are mesoporous, acidic ion exchangers based on divinylbenzene/styrene copolymers. The catalyst can be used in the dry or moist state. Acidic groups used are preferably sulphonic acid groups. The catalyst is prepared, for example, by copolymerization of styrene with divinylbenzene and sulphonation using sulphuric acid/oleum.

The process of the invention can be carried out, in a preferred way, continuously, batchwise or semi-batchwise.

In a preferred embodiment the reaction is implemented in a stirred tank, a stirred-tank cascade, a flow tube, one or more fixed-bed reactors, or a column. The catalytic reaction is carried out over a heterogeneous catalyst.

For the implementation of the process of the invention the starting substances, aromatic amine and aldehyde, are mixed continuously or discontinuously. The catalytic reaction then takes place at temperatures in the range from 80 to 140° C. Thereafter the isomer mixture of the bis(aminophenyl)alkanes is isolated by customary separation methods.

The catalyst has acidic centers, measured in accordance with DIN 54 403, in a concentration of 2 to 6 eq/kg.

The average pore diameter of catalyst particles, measured in accordance with ASTM D 4222, is 10 to 32 nm.

The examples below illustrate the invention.

EXAMPLES

1.

93.1 g of aniline and 10 g of the moist ion-exchange resin Amberlyst 35Wet, containing sulphone groups, were brought together under an $N_2$ atmosphere in a stirred container and were heated to 120° C. with stirring. At this temperature 8.1 g of formaldehyde solution (37% by weight formaldehyde in water), corresponding to an aniline/formalin molar ratio of 10:1, were metered in over the course of 60 minutes. The ion-exchange resin used has a concentration of acidic centres, according to the manufacturer's product datasheet, of at least 5.2 eq/kg and an average pore diameter of 300 Å (corresponding to 30 nm).

The composition of the reaction product (analysis by gas chromatography following removal of the aniline present in excess) is as follows: 0.9% by weight 2,2 MDA; 16.8% by weight 2,4 MDA; 70.6% by weight 4,4 MDA; 0.06% by weight N-methyl MDA and 11.7% by weight polynuclear compounds. The yield was 88.2% by weight.

2.

93.1 g of aniline and 10 g of the moist ion-exchange resin Amberlyst 39Wet, containing sulphone groups, were brought together under an $N_2$ atmosphere in a stirred container and were heated to 120° C. with stirring. At this temperature 8.1 g of formaldehyde solution (37% by weight formaldehyde in water), corresponding to an aniline/formalin molar ratio of 10:1, were metered in over the course of 60 minutes. The ion-exchange resin used has a concentration of acidic centres, according to the manufacturer's product datasheet, of at least 5.0 eq/kg and an average pore diameter of 230 Å (corresponding to 23 nm).

The composition of the reaction product (analysis by gas chromatography following removal of the aniline present in excess) is as follows: 1.5% by weight 2,2 MDA; 17.9% by weight 2,4 MDA; 66.8% by weight 4,4 MDA; 0.06% by weight N-methyl MDA and 13.8% by weight polynuclear compounds. The yield was 86.1% by weight.

3.

93.1 g of aniline and 10 g of the moist ion-exchange resin Amberlyst 70Wet, containing sulphone groups, were brought together under an $N_2$ atmosphere in a stirred container and were heated to 120° C. with stirring. At this temperature 8.1 g of formaldehyde solution (37% by weight formaldehyde in water), corresponding to an aniline/formalin molar ratio of 10:1, were metered in over the course of 60 minutes. The ion-exchange resin used has a concentration of acidic centres, according to the manufacturer's product datasheet, of at least 2.55 eq/kg and an average pore diameter of 220 Å (corresponding to 22 nm).

The composition of the reaction product (analysis by gas chromatography following removal of the aniline present in excess) is as follows: 1.1% by weight 2,2 MDA; 15.9% by weight 2,4 MDA; 69.4% by weight 4,4 MDA; 0.03% by weight N-methyl MDA and 13.6% by weight polynuclear compounds. The yield was 86.3% by weight.

The examples show that the required isomer ratio can be generated without further purification or distillation steps. The selectivity (S) of the reaction is calculated from the ratio between the amount of substance of the desired product (P) formed (in this case the sum of the 2,2', 2,4' and 4,4' isomers of MDA) and the amount of substance of the key component (K) reacted (in this case formaldehyde), taking into account the stoichiometric numbers (v). For batch operation, therefore:

$$S_P = \frac{n^0}{n_K^0 - n_K} \cdot \frac{|v_K|}{v_P} \cdot 100$$

After the stated number of minutes the full conversion of the formaldehyde employed was achieved. Accordingly the selectivity of the reaction is identical with the yield.

The invention claimed is:

1. A process for preparing at least one bis(aminophenyl)alkane in a catalytic reaction, comprising reacting an aromatic amine, which may be substituted or unsubstituted, with a $C_1$-$C_3$ aldehyde in the presence of a heterogeneous catalyst, wherein:
the catalyst is a mesoporous acidic ion exchanger based on a divinylbenzene/styrene copolymer;
the catalyst has acidic centers, measured in accordance with DIN 54 403, in a concentration of 2 to 6 eq/kg;
an average pore diameter of catalyst particles, measured in accordance with ASTM D 4222, is 10 to 32 nm, and
a polynuclear compound content of a reaction mixture formed is >10% and ≤15% by weight and
N methyl compounds content is ≤1% by weight.

2. The process according to claim 1, wherein formaldehyde is employed as the aldehyde.

3. The process according to claim 1, wherein aniline is the aromatic amine.

4. The process according to claim 1, wherein bis(aminophenyl)methane is prepared.

5. The process according to claim 1, wherein a isomer ratio of the bis(aminophenyl)alkane obtained is distributed as follows:

| | |
|---|---|
| 64% to 85% by weight | 4,4' diaminodiphenylalkane, |
| 3% to 20% by weight | 2,4' diaminodiphenylalkane, and |
| ≥1.0% to ≤2% by weight | 2,2' diaminodiphenylalkane. |

6. The process according to claim 5, wherein the isomer ratio of bis(aminophenyl)alkane obtained is distributed as follows:

| | |
|---|---|
| 64% to 85% by weight | 4,4' diaminodiphenylmethane, |
| 3% to 20% by weight | 2,4' diaminodiphenylmethane, and |
| ≥1.0% to ≤2% by weight | 2,2' diaminodiphenylmethane. |

7. The process according to claim 1, wherein a reaction temperature of the catalytic reaction is in a range from 80 to 140° C.

8. The process according to claim 1, wherein a reaction time for the catalytic reaction is 30 min to 5 hours.

9. The process according to claim 1, wherein a molar ratio of amine to aldehyde is 5:1 to 15:1.

10. The process according to claim 1, wherein the catalyst is employed in dry or moist form.

11. The process according to claim 1, wherein the process is carried out continuously, batchwise, or semi-batchwise.

12. The process according to claim 1, wherein the reaction is carried out in a stirred tank, a stirred-tank cascade, a flow tube, a fixed-bed reactor, or in a column.

13. The process according to claim 1, wherein sulfonic acid groups are employed as acidic centers for the catalyst.

14. The process according to claim 1, wherein a concentration of the acidic centers of the mesoporous acidic ion exchanger is 4.4 to 5.7 eq/kg, measured in accordance with DIN 54 403.

15. The process according to claim 1, wherein the pore diameter of the ion exchanger, measured in accordance with ASTM D 4222, is 15 up to and including 30 nm.

16. The process according to claim 1, wherein reaction temperature of the catalytic reaction is in a range from 80 to 130° C.

17. The process according to claim 1, wherein a concentration of the acidic centers of the mesoporous acidic ion exchanger is 4.7 to 5.6 eq/kg, measured in accordance with DIN 54 403.

18. The process according to claim 1, wherein the pore diameter of the ion exchanger, measured in accordance with ASTM D 4222, is 22 up to and including 30 nm.

19. The process according to claim 1, wherein the diaminodiphenylalkane is produced in a yield of 80 to 95%.

20. The process according to claim 1, wherein the N methyl compounds content is ≤0.5% by weight.

21. The process according to claim 1, wherein the N methyl compounds content is ≤0.3% by weight.

22. The process according to claim 1, wherein the N methyl compounds content is ≤0.06% by weight.

23. The process according to claim 1, wherein the N methyl compounds content is ≤0.03% by weight.

* * * * *